United States Patent
Liu et al.

(10) Patent No.: US 8,084,065 B2
(45) Date of Patent: Dec. 27, 2011

(54) COMPOSITIONS FOR TREATING AND PREVENTING HYPERLIPIDEMIA

(75) Inventors: Juan Liu, Jiangsu (CN); Shengmin Wu, Jiangsu (CN)

(73) Assignee: Fenchem Enterprises, Ltd, Nanjing Jiangsu (CN)

( * ) Notice: Subject to any disclaimer, the term of this patent is extended or adjusted under 35 U.S.C. 154(b) by 452 days.

(21) Appl. No.: 12/302,193

(22) PCT Filed: May 29, 2006

(86) PCT No.: PCT/CN2006/001125
§ 371 (c)(1),
(2), (4) Date: Nov. 24, 2008

(87) PCT Pub. No.: WO2007/137449
PCT Pub. Date: Dec. 6, 2007

(65) Prior Publication Data
US 2009/0181925 A1    Jul. 16, 2009

(51) Int. Cl.
*A61K 36/89* (2006.01)
*A61K 36/00* (2006.01)

(52) U.S. Cl. ........................ 424/750; 424/725

(58) Field of Classification Search .................. None
See application file for complete search history.

(56) References Cited

U.S. PATENT DOCUMENTS

| | | | |
|---|---|---|---|
| 6,126,943 A * | 10/2000 | Cheruvanky et al. | 424/750 |
| 6,248,378 B1 * | 6/2001 | Ganan-Calvo | 426/89 |
| 6,303,586 B1 * | 10/2001 | McPeak et al. | 514/54 |
| 6,565,896 B1 | 5/2003 | Gorsek | |
| 6,610,320 B2 | 8/2003 | Schmitz et al. | |
| 6,638,971 B2 * | 10/2003 | Romanczyk et al. | 514/456 |
| 7,683,095 B2 * | 3/2010 | Guthrie et al. | 514/456 |
| 2002/0054924 A1 * | 5/2002 | Leahy et al. | 424/732 |
| 2002/0160060 A1 * | 10/2002 | Chen et al. | 424/757 |
| 2006/0078533 A1 * | 4/2006 | Omoigui | 424/78.14 |
| 2006/0148733 A1 * | 7/2006 | Zhang et al. | 514/33 |
| 2009/0181925 A1 * | 7/2009 | Liu et al. | 514/54 |

FOREIGN PATENT DOCUMENTS

| | | |
|---|---|---|
| CN | 1559420 A | 1/2005 |
| CN | 1596907 A | 3/2005 |

OTHER PUBLICATIONS

English Abstracts for cited foreign references.

* cited by examiner

*Primary Examiner* — Christopher R. Tate
(74) *Attorney, Agent, or Firm* — Thomas, Kayden, Horstemeyer & Risley, LLP

(57) ABSTRACT

A composition for treatment and prevention of hyperlipidemia consists of phytosterols and phytostanols 30-50%, flavones derived from bamboo leaf 20-40%, procyanidins 10-25% and β-glucan of 5-20% by weight. Said composition demonstrates markedly therapeutic effects on preventing and treating hyperlipidemia, compared with the combinations of two or three components selected from phytosterols or phytostanols, flavones derived from bamboo leaf, procyanidins and β-glucan. When applied in supplementary nutrient foods or medicaments, the present composition can effectively lower the levels of cholesterol and triglyceride in blood, therefore can be useful for treating and preventing hyperlipidemia, cardiovascular diseases, coronary heart disease, atherosclerosis, heart disease and the like.

8 Claims, 1 Drawing Sheet

COMPOSITIONS FOR TREATING AND PREVENTING HYPERLIPIDEMIA

CROSS-REFERENCE TO RELATED APPLICATION

This application claims priority to PCT Application No. PCT/CN2006/001125, filed May 29, 2006 and entitled "COMPOSITIONS FOR TREATING AND PREVENTING HYPERLIPIDEMIA".

FIELD OF THE INVENTION

The present invention relates to prevention and treatment of hyperlipidemia, and particularly relates to treatment and prevention of hyperlipidemia using a composition of phytosterols, flavones derived from bamboo leaf, procyanidins and β-glucan.

BACKGROUND OF THE INVENTION

Blood lipids mainly refer to cholesterol and triglyceride in serum. The increases of cholesterol level, triglyceride level or both are all called hyperlipidemia. Hyperlipidemia and hypercholesteremia play a major role in development of atherosclerosis, which are the main causes of blood vessel and heart diseases. The research on medicaments for lowering levels of cholesterol and low density lipoprotein has long been the main focus on R & D work of lipid-lowering drugs.

Phytosterols are one category of sterols, which have a basic core structure of a heterocyclic compound (non aromatic substance) formed by three C6 rings (different from benzene ring) and one C5 ring, are constituents of various tissues and cells, and bond with proteins to form lipoprotein and constitute various membranes of cells, such as cellular membrane, nuclear membrane, mitochondrial membrane, and endoplasmic reticulum membrane etc. From an aspect of structure, phytsterols have a very similar structure with that of cholesterol, and the difference is only in structure of a branch thereof. Phytosterols are mainly β-sitosterol, stigmasterol, and campesterol, etc. (see formula I). As phytosterols have similar structure with that of cholesterol, phytosterols, phytostanols, and their esters, they can compete with cholesterol in vivo for inhibiting its absorption in small intestine, reduce plasma cholesterol level, and have the function of lowering levels of total cholesterol and low density lipoprotein (LDL) by adding into special food useful as functional food.

Formula I

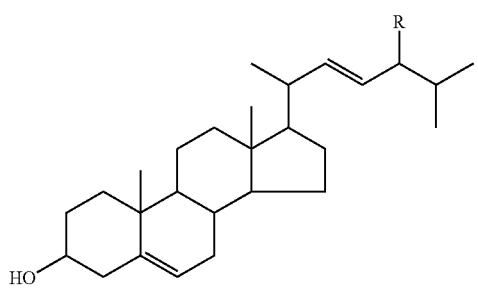

Bamboo leaf has long been used as medicine and food in China, which is a well known drug for clearing away heat and toxins in traditional Chinese medicine. A recent study shows that a bamboo leaf contains large amounts of flavones, phenolic acids, anthraquinones compounds, and bioactive polysaccharides, etc. Flavone glycosides are the main functional factors of bamboo leaf, which mainly comprise C-glycosides; the four main C-glycosylflavones (flavones derived from bamboo leaf) of bamboo leaf are respectively orientin, homoorientin, vitexin, and isoviextin. Studies have proved that flavones derived from bamboo leaf can significantly reduce the levels of triglycerides, total cholesterol, and low density lipoprotein (LDL) in the human body, and increase the level of high density lipoprotein (HDL), have functions of inhibiting lipid peroxidation, dilating coronary vessels, and inhibiting myocardial infarction, etc.

Procyanidins (PC) are the general name of a major category of polyphenol compounds, widely existing in plants, which are polymers formed by different amounts of catechin, epicatechin, or gallic acid linked together. A study shows that procyanidins are good oxygen free radical scavengers and lipid peroxidation inhibitor, have functions of protecting blood vessels, inhibiting atherosclerosis, platelet agglomeration, and myocardial ischemia, hypertension and regulating lipids, and receive more and more attention in the fields of nutrition and health care.

Glucan is a category of polysaccharides with glucose as the basic constituent unit, and is divided into two types, α-glucan and β-glucan. The natural glucan usually exists in form of β-glucan. β-glucan is a mixed linked glucan, whose molecular structure contains three glucoside bonds, β-1,3, β-1,4, and β-1,6, in which β-glucan of barley is β-1,3/1,4-glucan, can prevent and treat cardiovascular and cerebrovascular diseases caused by hyperlipidemia, and has functions of significantly reducing levels of lipid and serum cholesterol.

The aforementioned four kinds of substances respectively have certain effects on preventing and treating hyperlipidemia, cardiovascular diseases, coronary heart disease, atherosclerosis, and the like. Research on whether more effective treatment and prevention of hyperlipidemia can be achieved by using their combination has been done. From the available literature, most literature disclose compositions consisting of only two kinds of the aforementioned substances, for example US2003068357, WO03105600, WO2005072761, and WO0130359 have disclosed an extract or a composition containing phytosterols and β-glucan which can influence cholesterol level, and US2005227930 has disclosed a composition at least containing flavones derived from citrus, phytosterols or phytostanols which can lower cholesterol level. But until now, there is no report related to the composition of the present invention, and more effective products capable of achieving better synergistic effects need to be developed. After repeated research work and verification, the inventor of the present invention has finally found the composition capable of more effectively treating and preventing hyperlipidemia in order to complete the present invention.

SUMMARY OF THE INVENTION

The object of the present invention is to provide a composition capable of more effectively treating and preventing hyperlipidemia.

The composition of the present invention selects phytosterols, flavones derived from bamboo leaf, procyanidins and β-glucan for combination to achieve synergistic effects among the components, so as to more effectively treat and prevent hyperlipidemia. Phytosterols only have inhibition effects on absorption of cholesterol acquired from food, and have no effects on cholesterol produced by liver which is the main cause of high cholesterol. While flavones derived from bamboo leaf, procyanidins and β-glucan are mainly capable of reducing cholesterol produced by liver, the combination of the four kinds of compounds can achieve synergistic effect, and lower levels of cholesterol and triglycerides derived from food and produced by the liver in the human body, so as to reduce lipid level.

The amount of composition in the present invention is obtained through large amounts of experiments by the inventor, and desirable treatment effects can be achieved by amounts of each component within the following mass percentage range:
phytosterols or phytostanols 30-50%, flavones derived from 20-40% bamboo leaf, 10-25% procyanidins, and 5-20% β-glucan.

The preferred composition of the component is: 30% phytosterols or phytostanols, 40% flavones derived from bamboo leaf, 20% procyanidins, and 10% β-glucan.

Another preferred composition is: 50% phytosterols or phytostanols, 20% flavones derived from bamboo leaf, 25% procyanidins, and 5% β-glucan.

The most preferred scheme of the present invention is: the composition consists of 40% phytosterols or phytostanols, 30% flavones derived from bamboo leaf, 10% procyanidins, and 20% β-glucan. The treatment effect achieved by the scheme is more remarkable, and will be explained in detail below.

Each component of the composition according to present invention can be obtained and prepared by the method and step that are well known in the field.

Preferably, said phytosterols are obtained from deodorized soybean oil through extraction and separation. The phytosterols are selected from at least one of β-sitosterol, stigmasterol, and campesterol. The phytostanols are obtained from phytosterols through hydrogenation.

The flavones derived from bamboo leaf are C-glycosylflavones extracted from bamboo leaf.

The procyanidins can be extracted from plants like grape seed or guava.

The β-glucan is β-1,3/1,4-glucan, which can be extracted from plants like barley, oat, or rye.

The composition according to present invention is prepared by fully mixing the components according to the aforementioned mass percentage.

Compositions according to present invention are prepared by mixing phytosterols or phytostanols, and one or two of the other three components at various ratios and are subjected to clinical trial to compare their treatment effects of hyperlipidemia with those of the proceeding and phytosterols. The results show that the composition of the present invention has the best treatment effect for hyperlipidemia. By applying the composition of the present invention to nutrient supplement and medicament, synergistic effects can be achieved to prevent and treat hyperlipidemia, cardiovascular diseases, coronary heart disease, atherosclerosis, and the like.

DETAILED DESCRIPTION OF THE EMBODIMENTS

Figure 1:
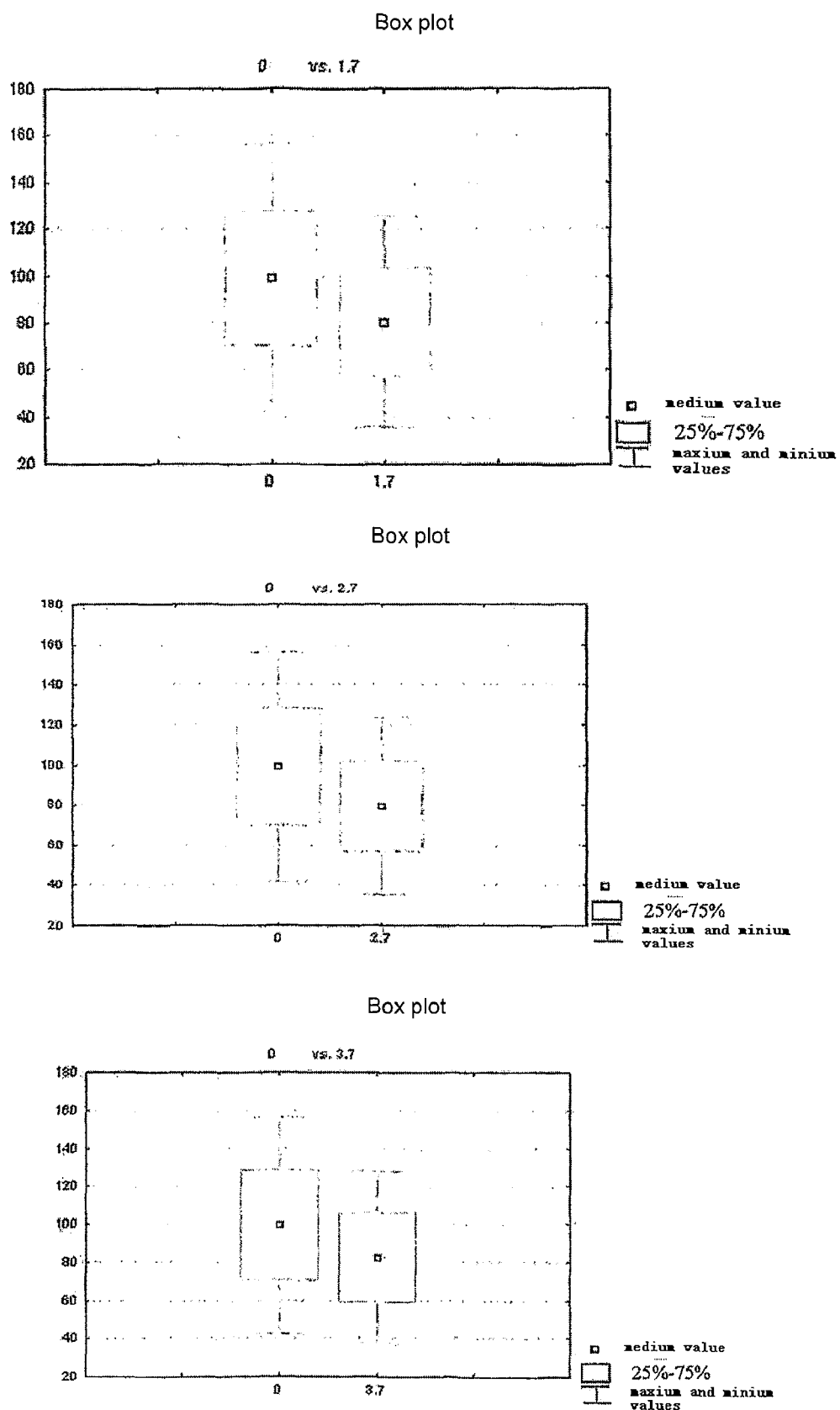
FIG. 1 is T-test analytical chart, in which 0 is the data before administration, 1.7, 2.7, and 3.7 are the datas for the composition of the present invention.

The terms adopted in the present invention usually have general meaning which is well known for those skill person in this area unless otherwise stated.

The term "phytosterols" used in the present invention includes at least one of β-sitosterol, stigmasterol, and campesterol. The term "phytostanols" refers to saturated or hydrogenated phytosterols. It should be understood that the term "phytosterols" includes phytosterols and phytostanols in the case of uncertainty in the descriptions, i.e. the two terms are mutually replaceable, unless specified otherwise.

Phytosterols, flavones derived from bamboo leaf, procyanidins and β-glucan in the following embodiments are prepared through known methods in the present invention, for example the preparation method of phytosterols refers to "Purification and recovery processes of phytosterols from deodorizer distillates" (Xu Wenlin, Wang Yaqiong, Lu Ping, The Chinese Journal of Process Engineering, Vol. 2, No. 2, April 2002); the preparation method of flavones derived from bamboo leaf refers to "Studies on the productive technology of flavonoids extract from the leaves of Phyllostachys pubescens" (Li Hongyu, Sun Jingyun, Dai Shiwen, The Chinese Journal of Modern Applied Pharmacy, Vol. 21, No. 5, October 2004); the preparation method of procyanidins refers to "Research on extract technology of grape seed polyphenol extract" (Li Hua, Wang Weixin, Yuan Chunlong, Food Research and development, Vol. 26, No. 6, 2005); the preparation method of β-glucan refers to "Studies on 'Water Method' Isolation and Characterization of Tibetan Hulless Barley B2-glucan" (Zeng Yu, Zhang Beichuan, Yan Fang, Tang Lin, Chen Fang, Journal of Sichuan University (Natural Science Edition), Vol. 40, No. 2, April 2003).

Embodiment 1

Clinical Observation of Treatment and Prevention of Hyperlipidemia Using the Composition of the Present Invention Phytosterols, flavones derived from bamboo leaf, procyanidins and β-glucan are prepared according to routine methods, and the various components are then fully mixed according to components and mass ratios in Table 1 into eight compositions of A1-A8:

TABLE 1

| Composition | Phytosterols (%) | flavones derived from bamboo leaf (%) | procyanidins (%) | β-glucan (%) |
| --- | --- | --- | --- | --- |
| A1 | 30 | 70 | 0 | 0 |
| A2 | 30 | 0 | 70 | 0 |
| A3 | 30 | 0 | 0 | 70 |
| A4 | 30 | 35 | 35 | 0 |
| A5 | 30 | 35 | 0 | 35 |
| A6 | 30 | 0 | 35 | 35 |
| A7 (Composition of the present invention) | 30 | 40 | 20 | 10 |
| A8 | 100 | 0 | 0 | 0 |

80 Trial subjects are selected and divided into 8 groups, each of which consisted of 10 trial subjects. The total cholesterol level of each trail subject is above 210 mg/dL, low density lipoprotein (LDL) is above 140 mg/dL, and triglyceride is less than 300 mg/dL. All the trial subjects have similar other health conditions, stop administration of any lipid-lowering drugs and nutrient supplement before one month for the trial, and have identical dietary during the trial period. The trial subjects of the eight groups are respectively administered with the aforementioned eight compositions at 200 mg per day. After the compositions are administered for six weeks, the trial subjects are tested for total cholesterol (TC), low density lipoprotein (LDL), high density lipoprotein (HDL), triglycerides (TG), and systolic blood pressure (SBP) and diastolic blood pressure (DBP), and the data is shown in Table 2.

TABLE 2

Treatment effect indicator improvement after six weeks of treatment using the A1-A8 compositions

| Indicator | | (TC) (mg/dL) | (LDL) (mg/dL) | (HDL) (mg/dL) | (TG) (mg/dL) | (SBP) (mmHg) | (DBP) (mmHg) |
|---|---|---|---|---|---|---|---|
| Before administration | | 230.12 ± 20.26 | 162.50 ± 25.65 | 45.26 ± 12.51 | 66.23 ± 36.50 | 111.2 ± 20.32 | 78.50 ± 12.63 |
| After administration | A1 | 217.77 ± 23.56 | 159.15 ± 22.10 | 45.59 ± 11.52 | 63.02 ± 29.99 | 108.66 ± 20.33 | 78.00 ± 12.79 |
| | A2 | 218.25 ± 25.22 | 160.01 ± 22.19 | 45.47 ± 12.50 | 64.98 ± 31.25 | 109.1 ± 20.00 | 78.27 ± 12.01 |
| | A3 | 221.9 ± 25.78 | 160.99 ± 23.22 | 45.36 ± 12.24 | 65.37 ± 30.17 | 111.02 ± 19.21 | 78.38 ± 12.50 |
| | A4 | 194.98 ± 21.15 | 145.00 ± 20.15 | 46.68 ± 10.56 | 51.18 ± 30.57 | 106.90 ± 19.54 | 77.39 ± 11.43 |
| | A5 | 195.85 ± 20.09 | 145.44 ± 19.89 | 46.52 ± 11.22 | 52.19 ± 30.23 | 107.00 ± 19.47 | 77.46 ± 11.57 |
| | A6 | 198.02 ± 20.11 | 148.21 ± 19.81 | 46.22 ± 10.85 | 55.46 ± 29.96 | 107.37 ± 20.79 | 77.61 ± 11.00 |
| | A7 | 183.19 ± 20.15 | 123.35 ± 22.56 | 50.55 ± 11.52 | 36.58 ± 20.57 | 96.1 ± 18.22 | 70.01 ± 10.12 |
| | A8 | 200.12 ± 19.80 | 153.01 ± 21.07 | 46.09 ± 10.87 | 57.53 ± 30.44 | 107.51 ± 19.15 | 77.68 ± 10.64 |

The above trial results show that there are different treatment effects among different compositions, phytosterols play a major role in reducing cholesterol level, and flavones derived from bamboo leaf are second to them. When phytosterols are compounded with the other components, their function changes to various extents. The synergistic effect is not desirable when phytosterols are mixed only with one of the other components (A1, A2, and A3); but when phytosterols are mixed with two or three of the other components (A4-A7), the synergistic effects are significantly better than that of single phytosterols, especially the treatment effect of combination of four of the components is the best, which can lower total cholesterol level by 28%, and lower low density lipoprotein level by 24%.

Embodiment 2

Clinical Observation of Treatment and Prevention of Hyperlipidemia Using the Compositions of the Present Invention Phytosterols derived from soybean, flavones derived from bamboo leaf, procyanidins and β-glucan (β-1,3/1,4-glucan) are prepared according to routine methods, and which are then prepared into eight compositions B1-B8 according to components and mass percentages in Table 3, wherein the B7 is the composition of the present invention.

TABLE 3

| Composition | Phytosterols (%) | flavones derived from bamboo leaf (%) | procyanidins (%) | β-glucan (%) |
|---|---|---|---|---|
| B1 | 40 | 60 | 0 | 0 |
| B2 | 40 | 0 | 60 | 0 |
| B3 | 40 | 0 | 0 | 60 |
| B4 | 40 | 30 | 30 | 0 |
| B5 | 40 | 30 | 0 | 30 |
| B6 | 40 | 0 | 30 | 30 |
| B7 (Composition of the present inventionn) | 40 | 30 | 10 | 20 |
| B8 | 100 | 0 | 0 | 0 |

80 Trial subjects are selected and divided into 8 groups, each of which consists of 10 trial subjects. The total cholesterol level of each trail subject is above 210 mg/dL, low density lipoprotein (LDL) is above 140 mg/dL, and triglyceride is less than 300 mg/dL. All the trial subjects have similar other health conditions, stop administration of any lipid-lowering drugs and nutrient supplement before one month for the trial, and have identical dietary during the trial period. The trial subjects of the eight groups are respectively administered with the aforementioned eight compositions at 200 mg per day. After the compositions are administered for six weeks, the trial subjects are tested for total cholesterol (TC), low density lipoprotein (LDL), high density lipoprotein (HDL), triglycerides (TG), and systolic blood pressure (SBP) and diastolic blood pressure (DBP), and the data is shown in Table 4.

TABLE 4

Treatment effect indicator improvement after six weeks of treatment using the B1-B8 compositions

| Indicator | | (TC) (mg/dL) | (LDL) (mg/dL) | (HDL) (mg/dL) | (TG) (mg/dL) | (SBP) (mmHg) | (DBP) (mmHg) |
|---|---|---|---|---|---|---|---|
| Before administration | | 230.12 ± 20.26 | 162.50 ± 25.65 | 45.26 ± 12.51 | 66.23 ± 36.50 | 111.2 ± 20.32 | 78.50 ± 12.63 |
| After administration | B1 | 207.01 ± 20.13 | 154.90 ± 22.93 | 45.80 ± 10.22 | 60.03 ± 29.79 | 108.02 ± 19.36 | 77.86 ± 10.97 |
| | B2 | 208.55 ± 22.12 | 156.79 ± 24.25 | 45.74 ± 10.56 | 61.68 ± 30.02 | 108.10 ± 20.10 | 77.90 ± 11.23 |
| | B3 | 209.12 ± 20.19 | 157.21 ± 23.01 | 45.62 ± 10.73 | 62.13 ± 29.21 | 108.23 ± 19.98 | 77.95 ± 11.78 |
| | B4 | 189.19 ± 20.78 | 139.91 ± 20.35 | 47.19 ± 11.25 | 47.78 ± 30.56 | 105.97 ± 19.38 | 76.89 ± 11.21 |
| | B5 | 190.22 ± 21.56 | 141.17 ± 20.03 | 47.07 ± 11.01 | 48.20 ± 30.47 | 106.15 ± 20.47 | 77.02 ± 10.56 |
| | B6 | 197.90 ± 21.03 | 147.55 ± 20.01 | 46.36 ± 11.57 | 51.01 ± 30.12 | 107.15 ± 20.38 | 77.55 ± 12.34 |
| | B7 | 181.32 ± 21.20 | 110.74 ± 20.11 | 51.30 ± 12.89 | 34.43 ± 16.11 | 95.89 ± 18.37 | 68.52 ± 10.34 |
| | B8 | 200.02 ± 19.99 | 151.90 ± 20.15 | 46.04 ± 10.78 | 57.04 ± 31.24 | 107.55 ± 19.78 | 77.70 ± 10.56 |

The above trial results show that there are different treatment effects among different compositions. When phytosterols are compounded with the other components, their function changes to various extents. The synergistic effect is not desirable when phytosterols are mixed only with one of the other components (B1-B3); but when phytosterols are mixed with two or three of the other components (B4-B7), the synergistic effects are significantly better than that of single phytosterols, especially the treatment effect of combination (the inventive composition B7) of four of the components is the best, which can lower total cholesterol level by about 39%, and lower low density lipoprotein level by about 32%.

Embodiment 3

Clinical Observation of Treatment and Prevention of Hyperlipidemia Using the Composition of the Present Invention Phytosterols, flavones derived from bamboo leaf, procyanidins and β-glucan are prepared according to routine methods, and which are then prepared into eight compositions C1-C8 according to components and mass ratios in Table 5.

TABLE 5

| Compositions | Phytosterols (%) | flavones derived from bamboo leaf (%) | procyanidins (%) | β-glucan (%) |
|---|---|---|---|---|
| C1 | 50 | 50 | 0 | 0 |
| C2 | 50 | 0 | 50 | 0 |
| C3 | 50 | 0 | 0 | 50 |
| C4 | 50 | 40 | 10 | 0 |
| C5 | 50 | 40 | 0 | 10 |
| C6 | 50 | 0 | 40 | 10 |
| C7 (Composition of the present invention) | 50 | 20 | 25 | 5 |
| C8 | 100 | 0 | 0 | 0 |

80 Trial subjects are selected and divided into 8 groups, each of which consists of 10 trial subjects. The total cholesterol level of each trial subject is above 210 mg/dL, low density lipoprotein (LDL) is above 140 mg/dL, and triglycerides is less than 300 mg/dL. All the trial subjects have similar other health conditions, stop administration of any lipid-lowering drugs and nutrient supplement before one month for the trial, and have identical dietary during the trial period. The trial subjects of the eight groups are respectively administered with the aforementioned eight compositions at 200 mg per day. After the compositions are administered for six weeks, the trial subjects are tested for total cholesterol (TC), low density lipoprotein (LDL), high density lipoprotein (HDL), triglycerides (TG), and systolic blood pressure (SBP) and diastolic blood pressure (DBP), and the data is shown in Table 6.

TABLE 6

Treatment effect indicator improvement after six weeks of treatment using the C1-C8 compositions

| Indicator | | (TC) (mg/dL) | (LDL) (mg/dL) | (HDL) (mg/dL) | (TG) (mg/dL) | (SBP) (mmHg) | (DBP) (mmHg) |
|---|---|---|---|---|---|---|---|
| Before administration | | 230.12 ± 20.26 | 162.50 ± 25.65 | 45.26 ± 12.51 | 66.23 ± 36.50 | 111.2 ± 20.32 | 78.50 ± 12.63 |
| After administration | C1 | 198.79 ± 20.38 | 151.04 ± 20.78 | 46.16 ± 10.15 | 56.85 ± 30.00 | 107.50 ± 20.36 | 77.65 ± 11.02 |
| | C2 | 201.87 ± 19.98 | 153.55 ± 21.14 | 45.97 ± 10.33 | 57.97 ± 30.13 | 107.64 ± 19.97 | 77.73 ± 11.13 |
| | C3 | 206.71 ± 20.00 | 154.00 ± 20.76 | 45.89 ± 11.25 | 58.86 ± 30.14 | 107.93 ± 20.04 | 77.80 ± 11.01 |
| | C4 | 193.51 ± 20.07 | 143.53 ± 21.11 | 46.98 ± 10.57 | 49.34 ± 28.98 | 106.23 ± 20.37 | 77.11 ± 10.37 |
| | C5 | 194.10 ± 20.90 | 144.04 ± 20.04 | 46.80 ± 10.15 | 50.25 ± 29.56 | 106.55 ± 18.99 | 77.29 ± 10.79 |
| | C6 | 196.86 ± 20.15 | 146.54 ± 20.21 | 46.43 ± 10.79 | 53.77 ± 30.56 | 107.04 ± 20.56 | 77.50 ± 12.11 |
| | C7 | 187.22 ± 20.77 | 130.12 ± 21.21 | 47.89 ± 11.10 | 38.19 ± 21.34 | 97.32 ± 17.97 | 71.45 ± 10.21 |
| | C8 | 200.34 ± 20.01 | 152.57 ± 19.64 | 46.09 ± 10.44 | 57.58 ± 30.35 | 107.60 ± 19.12 | 77.67 ± 9.99 |

The above trial results show that there are different treatment effects among different compositions. When phytosterols are compounded with the other components, their function changes to various extents. The synergistic effect is not desirable when phytosterols are mixed only with one of the other components (C1-C3); but when phytosterols are mixed with flavones derived from bamboo leaf at the same ratio (C3), the treatment effect is better than that of single phytosterols but still lower than those of the compositions C4-C7, especially the treatment effect of the composition C7 of the present invention is the best, which can lower total cholesterol level by about 26%, and lower low density lipoprotein level by about 20%.

Embodiment 4

The aforementioned trial results are consolidated and analyzed by Statistic software, and the analytical datas are shown in Table 7, wherein 0.8 is 100% phytosterols, 1.x, 2.x, and 3.x are respectively seven compositions in the embodiment 1, 2, and 3. The Table 7 shows that the compositions A4, A5, and A7 in the embodiment 1, the compositions B4, B5, and B7 in the embodiment 2, and the composition C7 in the embodiment 3 show significant influence on treatment effect indicator levels of hyperlipidemia after administration, especially the inventive compositions A7, B7, and C7 of the present invention (see FIG. 1).

TABLE 7

| | T-test | |
|---|---|---|
| Variable | Standard variable | P value |
| 1.3 | 74.22891 | 0.298002 |
| 1.2 | 73.06035 | 0.204435 |
| 1.1 | 72.95518 | 0.136117 |
| 2.3 | 70.08382 | 0.178566 |
| 2.2 | 69.90697 | 0.169478 |
| 2.1 | 69.35320 | 0.143056 |
| 3.3 | 68.96152 | 0.146322 |
| 3.2 | 67.66104 | 0.151825 |
| 0.8 | 67.51731 | 0.118817 |
| 3.1 | 66.55177 | 0.140900 |
| 1.6 | 66.37436 | 0.111398 |
| 2.6 | 66.41657 | 0.102667 |
| 3.6 | 65.49546 | 0.118845 |

TABLE 7-continued

| Variable | T-test Standard variable | P value |
|---|---|---|
| 1.5 | 65.66848 | 0.097738 |
| 1.4 | 65.47012 | 0.095718 |
| 3.5 | 64.69565 | 0.106062 |
| 3.4 | 64.54825 | 0.101863 |
| 2.5 | 63.64977 | 0.095492 |
| 2.4 | 63.22516 | 0.093809 |
| 3.7 | 61.84116 | 0.048376 |
| 1.7 | 60.22315 | 0.047923 |
| 2.7 | 59.41613 | 0.049862 |

Embodiment 5

Phytosterols are hydrogenated into phytostanols, then the phytostanols are mixed with flavones derived from bamboo leaf, procyanidins and β-glucan respectively according to formulation schemes in the embodiments 1-3 to prepare into corresponding compositions. Clinical observation is carried out according to the method in the embodiments 1-3 to obtain similar results. Compared with other compositions, the composition of the present invention shows better treatment effect.

The invention claimed is:

1. A composition for treating hyperlipidemia or reducing the risk thereof, comprising: 30-50% by weight phytosterols or phytostanols, 20-40% by weight flavones derived from bamboo leaf, 10-25% by weight procyanidins, and 5-20% by weight β-glucan.

2. The composition according to claim 1, comprising 30% by weight phytosterols or phytostanols, 40% by weight flavones derived from bamboo leaf, 20% by weight procyanidins, and 10% by weight β-glucan.

3. The composition according to claim 1, comprising 50% by weight phytosterols or phytostanols, 20% by weight flavones derived from bamboo leaf, 25% by weight procyanidins, and 5% by weight β-glucan.

4. The composition according to claim 1, characterized by comprising 40% by weight phytosterols or phytostanols, 30% by weight flavones derived from bamboo leaf, 10% by weight procyanidins, and 20% by weight β-glucan.

5. The composition according to claim 1, wherein at least one of the phytosterols is selected from the group consisting of β-sitosterol, stigmasterol, and campesterol.

6. The composition according to claim 5, wherein the phytosterols are extracted from soybean.

7. The composition according to claim 5, wherein the β-glucan is β-1,3/1,4-glucan.

8. The composition according to claim 7, wherein the β-1,3/1,4-glucan is extracted from barley, oat, or rye.

* * * * *